United States Patent [19]

Saito

[11] Patent Number: 5,219,339
[45] Date of Patent: Jun. 15, 1993

[54] SINGLE USE MEDICAL NEEDLE

[76] Inventor: Masataka Saito, 3-11-5 Kitakokubu, Ichikawa-shi, Chiba-ken, Japan

[21] Appl. No.: 730,949
[22] PCT Filed: Nov. 16, 1990
[86] PCT No.: PCT/JP90/01501
 § 371 Date: Jul. 17, 1991
 § 102(e) Date: Jul. 17, 1991
[87] PCT Pub. No.: WO91/07196
 PCT Pub. Date: May 30, 1991

[30] Foreign Application Priority Data

Nov. 17, 1989 [JP] Japan .................................. 1-297422

[51] Int. Cl.⁵ ............................................. A61M 5/32
[52] U.S. Cl. .................... 604/198; 604/177; 604/263
[58] Field of Search ............... 604/110, 192, 198, 263, 604/171, 177, 197

[56] References Cited

U.S. PATENT DOCUMENTS

| 4,826,490 | 5/1989 | Byrne et al. | 604/198 |
| 4,842,586 | 6/1989 | Hogan | 604/192 |
| 4,878,902 | 11/1989 | Wanderer et al. | 604/192 |
| 5,011,479 | 4/1991 | Le et al. | 604/198 |

FOREIGN PATENT DOCUMENTS

229062 9/1988 Japan .
212561 8/1989 Japan .
5968 1/1990 Japan .

Primary Examiner—C. Fred Rosenbaum
Assistant Examiner—C. Maglione
Attorney, Agent, or Firm—Nixon & Vanderhye

[57] ABSTRACT

This invention relates to a medical needle used for injection, drip infusion, blood sampling, biopsy, puncture, examination, artificial dialysis, indwelling and so forth, and more particularly to a medical needle for single use such as a so-called disposable injection needle, has as its object the provision of a medical needle covering a wide range of safety before use, during use, and after use, and the needle comprises: a cannula having a sharp point; a supporting-connecting member for supporting the cannula and connecting the cannula to another functional member; and a cover member capable of being engaged with the supporting-connecting member, being movable back and forth in the lengthwise direction of the cannula and capable of covering the point of the cannula, in which cover member, a semi-stable position and a stable position are provided at a position for covering the point of the cannula, and, once the cover member fits in the stable position, it cannot move to any other position.

2 Claims, 13 Drawing Sheets

SINGLE USE MEDICAL NEEDLE

TECHNICAL FIELD

This invention is concerned with needles for medical uses such as those used in injection, infusion, blood collection, biopsy, puncture, examination, dialysis, and intra-venous retention, and more particularly with those for single use such as disposable injection needles.

BACKGROUND ART

Medical needles such as those used for injection, infusion, and blood collection generally possess sharp blade tips to puncture into skins of living bodies. Use of such needles in repetition is accompanied with risks of transmitting pathogens from a body to another, and it is now common that needles are used once and discarded.

There are, however, a number of people who handle the needles, including those who actually use the needles such as doctors and nurses, and those who handle the needles until final disposition of the needles. There is a potential danger that the needle tip accidentally injures the users before the use and particularly after the use, or accidentally injures those who handle the needles thereafter. The needles before use are sterile, but there arises risks of infection by transfer of pathogens through a medium such as blood when a needle is once used through the skin of a living body, and the tip then accidentally injures one or more other persons.

It is therefore desirable that such accidental puncturing is prevented throughout the life of needles from a time before the use until they are finally demolished. Needles for medical uses are generally distributed with their tips protected by caps. The caps are put on the tips again after the use for protecting the tips. It happens commonly, however, that the used needles are thrown away without the caps. The Japanese patent laid-open publication JPA62-72367 proposes safety devices for hypodermic needle or the like that connects a hypodermic needle with a sleeve. The sleeve slides along the needle after the use and is locked where the sleeve completely covers the needle.

As discussed in the foregoing, needles for medical uses bear a high risk of accidental puncturing from a time before the use until they are finally demolished.

DISCLOSURE OF INVENTION

An object of the present invention is to provide a medical needle that can be safely handled throughout the life from a time before the use until it is finally demolished.

The present invention provides a needle for medical use comprising of a cannula having a sharp blade tip, a supporting and connecting member holding said cannula and connecting with another functional member, and a cover member engaged with said supporting and connecting member, and being movable forward and backward along a longitudinal direction of the cannula, capable of covering said blade tip of the cannula, having a metastable position both at positions for covering said blade tip of the cannula, wherein when the cover member goes into the stabele position, it is no longer able to transfer to another position.

The cover member has meta-stable and stable positions that completely cover the blade tip of the cannula, and is able to protect the needle tip before the use at the meta-stable position, and after the use at the irreversible stable position.

As elaborated in the above, a needle for medical use according to the present invention can prevent accidental puncturing by having the covering member cover the sharp needle tip before and after the use, wherein it is in the meta-stable position before the use where the needle tip cannot be revealed unless it is intentionally handled, and it is in the locked (stable) position after the use.

The needle therefore makes it possible to keep a wide range of people, from the users like doctors and nurses to those finally demolish the needles, from being accidentally injured at the skin and getting infected with pathogens.

BRIEF DESCRIPTION OF DRAWINGS

FIGS. 10A to 10D, FIGS. 11A to 11E, and

The numbers in the drawings indicate the following: 1 body, 2 head, 3 first neck, 4 slant, 5 second neck, 6 broad body, 7 third neck, 8 bottom, 10 cap, 11 bore, 12 head of cap, 13, 45 flange, 14 slit, 20 needle part, 21 cannula, 22 supporting and connecting member, 23 wing member, 24 broad umbrella-like part, 29 broad body, 25, 28, 41 neck, 26, 27, 42 slant, 30 covering member, 31 opening, 33, 47 projection (engaging member), 36 tube (other functional member), 38, 43 rib, 44 holder, 46 gutter.

EMBODIMENTS

FIGS. 1A to 1F present an embodiment of the present invention applied to a needle for use with a syringe.

Figure 1A:
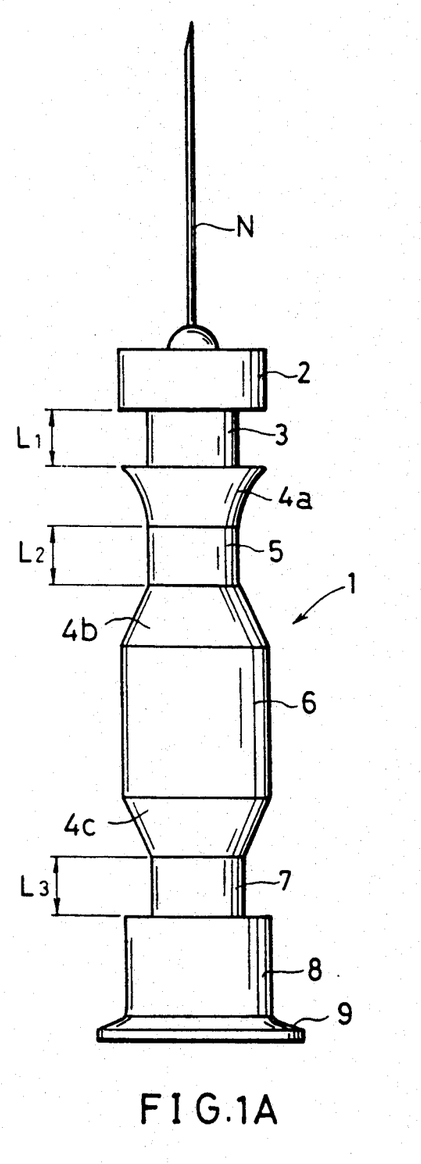
FIGS. 1A–1F show an embodiment of the present invention applied to an injection needle.
Figure 1B:
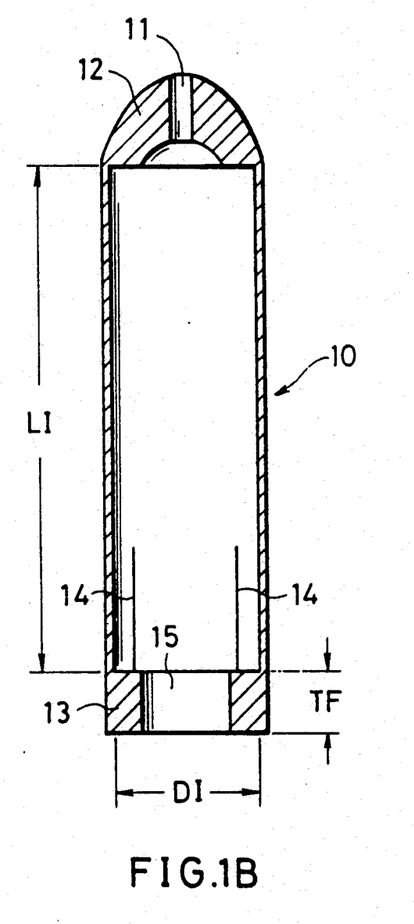
Figure 1C:
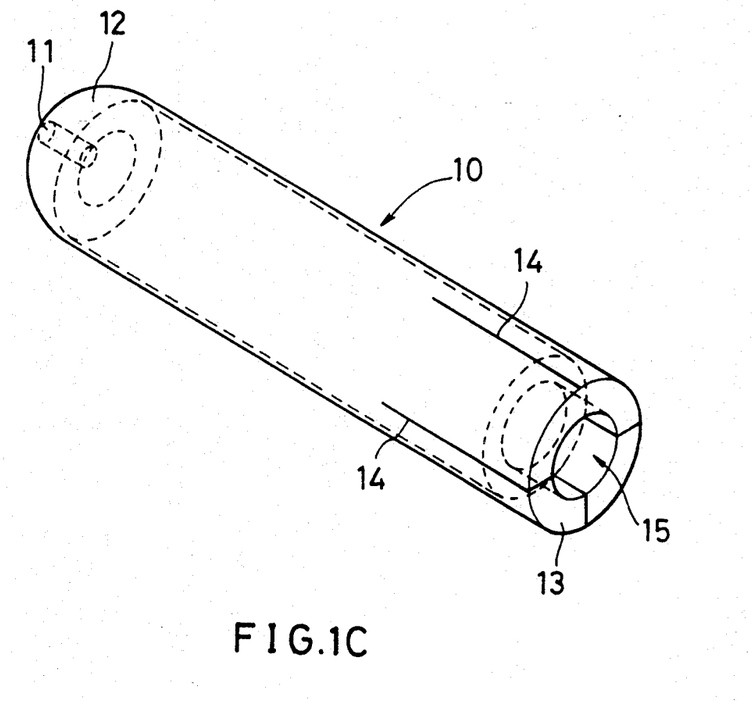

The needle comprises a needle part and a cap part shown respectively in FIGS. 1A and 1B.

The needle part in FIG. 1A comprises the cannula N and the body 1. The cannula N is for instance a stainless steel cannula with a length of about 13 to 38 mm an outer diameter of about 0.3 to 1.2 mm, and the point is ground slant to bear blades.

The body 1 has a passage in the central portion for allowing injection fluids to flow, and is made of such materials as plastics. The passage can be formed by making the material such as plastics in a hollow shape or by having the cannula N extended to the end. The body is columnar, and the external surface is made to consist of circumferential surfaces of different diameters. That is, in the drawing, the head 2 with the largest diameter, a little constricted first neck 3, the gradual slant 4a below the large circular spread, the second neck 5 with the constricted diameter, the slant 4b that expands downward from the second neck, the broad columnar body 6 having a large diameter, the slant 4c that gradually shrinks downward from the broad body 6, the constricted third neck 7, the bottom 8 having a large diameter for connection with a syringe, and a flange 9 to stabilize connection with syringe. Observing the three necks 3, 5, and 7, the first neck 3 has perpendicular sides at its top and bottom, the second neck 5 continues to slants at the both sides, and the third neck 7 has a slant at one side and a perpendicular side at the bottom.

The cap 10 has a sectional structure as shown in FIG. 1B. The head 12 of the cap 10 has smooth streamlined external surface and a bore 11 at the center to let the cannula N pass. The inside of the cap 10 is of columnar hollow structure to accomodate the body. A flange 13 is positioned at the opening 15 for engagement with the necks of the body. Slits may be formed along the longitudinal direction, as shown in the perspective view in FIG. 1C, to facilitate smooth sliding of the cap 10 over different diameters when the flange 13 is engaged with the body 1.

It is desirable the length of the necks $L_1$, $L_2$ and $L_3$ is made the same or slightly longer than the thickness of the flange TF. The inner diameter DI of the cap is made approximately the same as the outer diameter of the broad body 6 and the head 2. The length LI is made to be the same or a little longer than the length from the top of the head 2 to the upper end of the third neck 7, and the head of the cap 10 is so made to completely cover the cannula N when the flange 13 is engaged with the first neck 3 or the second neck 5. The internal surface of the flange 13 and the columnar external surface of the necks 3, 5, and 7 are made to be parallel with the longitudinal axis.

Figures 1D, 1E:
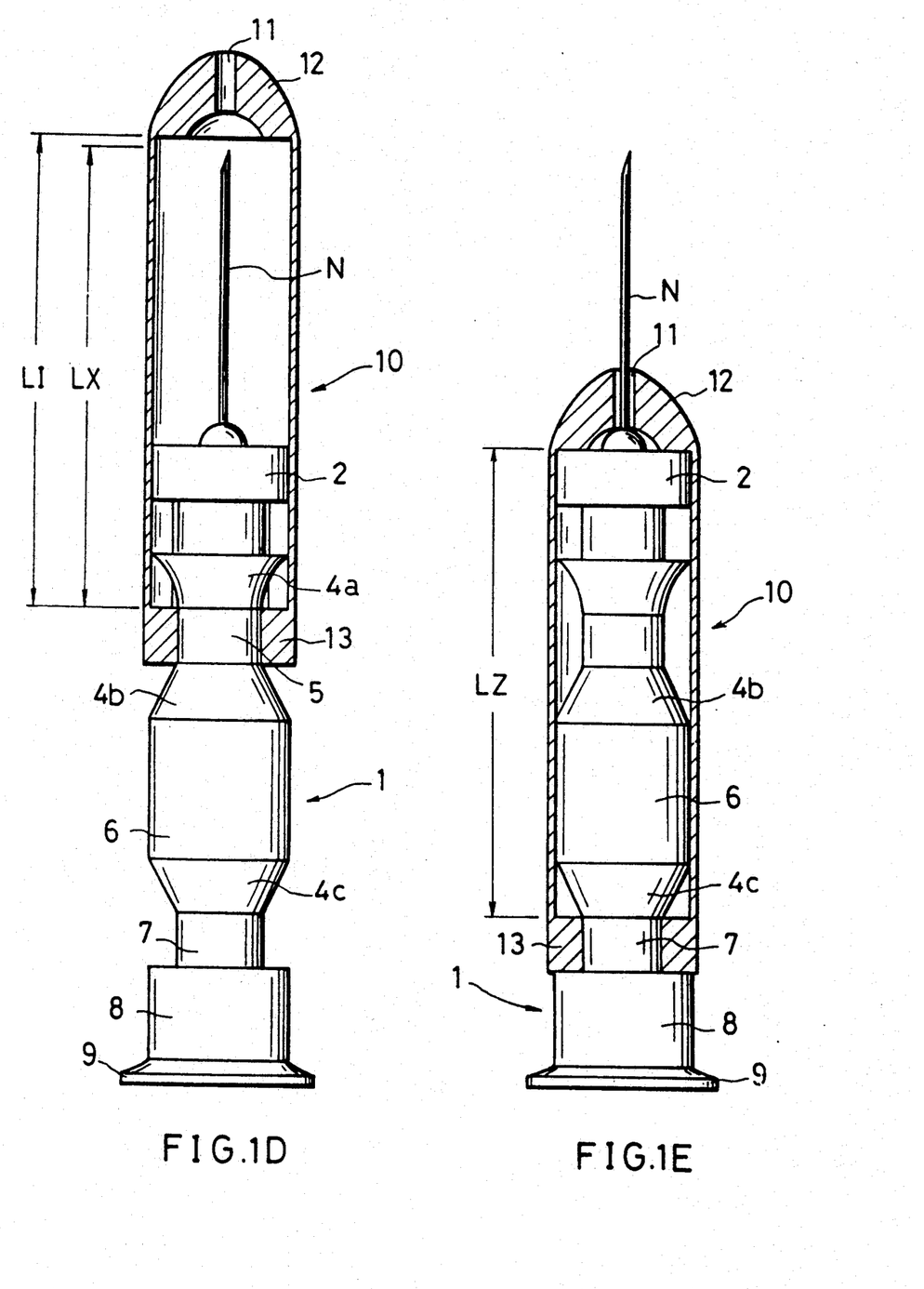
Figure 1F:
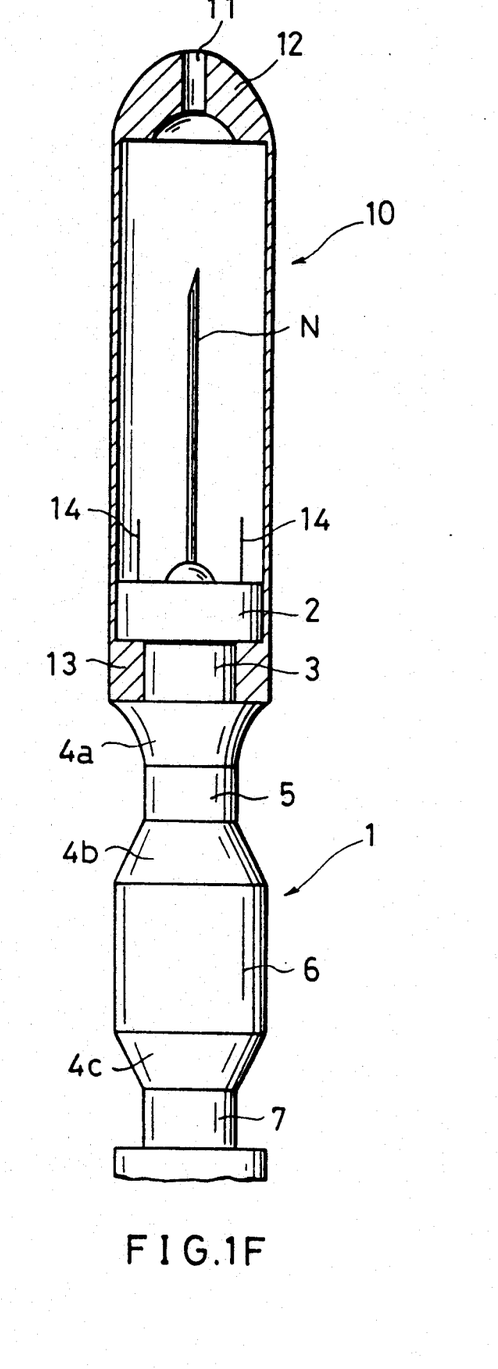

FIGS. 1D, 1E, and 1F present three states of the body engaged with the cap.

FIG. 1D shows the state of an unused needle in distribution from the manufacturing place to where it is used such as hospitals. The flange 13 of cap 10 is engaged with the second neck 5, and the cannula N is housed inside the hollow cap 10. The length LI of the columnar internal surface of cap 10 is made to be longer than the length LX between the tip of the cannula and the upper end of the second neck 5. The large circular spread of the slant 4 and the head 2 touch the inner surface of the hollow cap 10 to steadily hold the cap 10 together with the engagement at the flange 13. The slope at the slant 4a is so made to give proper resistance for the cap 10 to move into the first neck 3.

FIG. 1E shows the state to make use of the needle where it is in connection with a syringe. The cap 10 has moved over the slant 4b, the broad body 6, and the slant 4c to settle at the third neck 7. The internal surface of the head 12 of the cap 10 nearly touches the surface of the adhesive that holds the cannula N. The cannula N is projecting over the cap through the bore 11, and is ready to use. The length LI of the columnar inside surface of cap 10 is made the same as or a little longer than the length LZ that is from the top of the head 2 to the upper end of the third neck 7. Although not shown in the drawing, a syringe is connected to the internal surface of the bottom 8 and medical or other liquid goes through the connection.

Further, in this state, the internal surface of the flange 13 is engaged with the outer surface of the third neck 7. The large diameter portion 6 and the large diameter position of the slant 4 as well as the cylindrical surface of the head 2 touch the internal surface of the cap 10 to stabilized the cap 10.

FIG. 1F shows the stable position where the cap 10 is settled at the lock position after the injection needle is used. The cap 10 is slid as far upward as possible from where it was in FIG. 1E. That is, the flange 13 has slid from the third neck 7 to the slant 4c, and over to the large diameter portion 6, the slant 4b, the second neck 5, and then to the slant 4a to settle in the first neck 3. The surface of the first neck 3 is engaged with the internal surface of the flange 13, and the cylindrical surface of the head 2 touches the hollow internal surface of the cap 10.

The internal surface of the opening at flange 13 is flat and made parallel to the needle longitudinal axis. The internal surface is made approximately parallel to the external surface of the first neck 3, and the top and bottom sides of the flange 13 are made approximately vertical to the axis. Once the flange 13 moves into the first neck 3 therefore, the cap is no more able to transfer to another position. That is, the cap 10 is locked in this state.

The cannula N is shown in the Figure to stay inside the hollow cap 10. It is, however safe as long as the cannula N does not protrude out of the bore 11. The cannula N may hence be positioned to stay inside the bore 11.

It is preferable to make the cap by such an elastic material as polypropylene so that it may slide over the slant when connected to the body 1.

Figure 2:
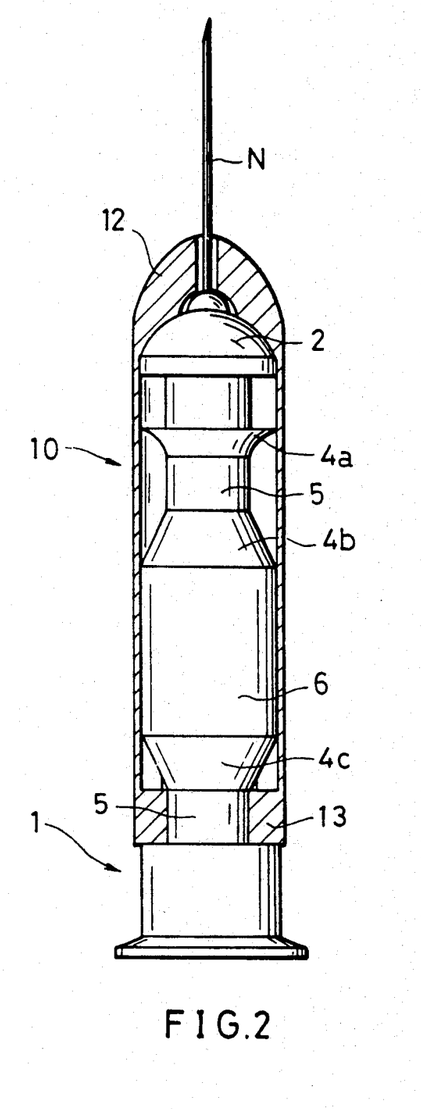
FIGS. 2 and 3 are partly sectional side views of other embodiments of the present invention applied also to injection needles.

FIG. 2 shows a needle according to another embodiment of the present invention. The head 2 of the body 1 is spherical in this example, and the inside of the head 12 of the cap 10 is also made spherical to receive the spherical head 2. By making the head 2 in such a shape, the needle can be more convenient in the manufacturing. That is, after the cap 10 and the body 1 are separately manufactured, it is possible to assemble the two units by dropping down the cap 10 onto the head 2 and pressing down when the flange 13 of the cap 10 opens as it slides down along the spherical head 2. Further, in case the bore 11 of the cap 10 is made so wide open as to have the head 2 exposed outside when the cap 10 is depressed to the most downward, a cannula N may be inserted and glued after the body 1 and the cap 10 are assembled.

Figure 3:
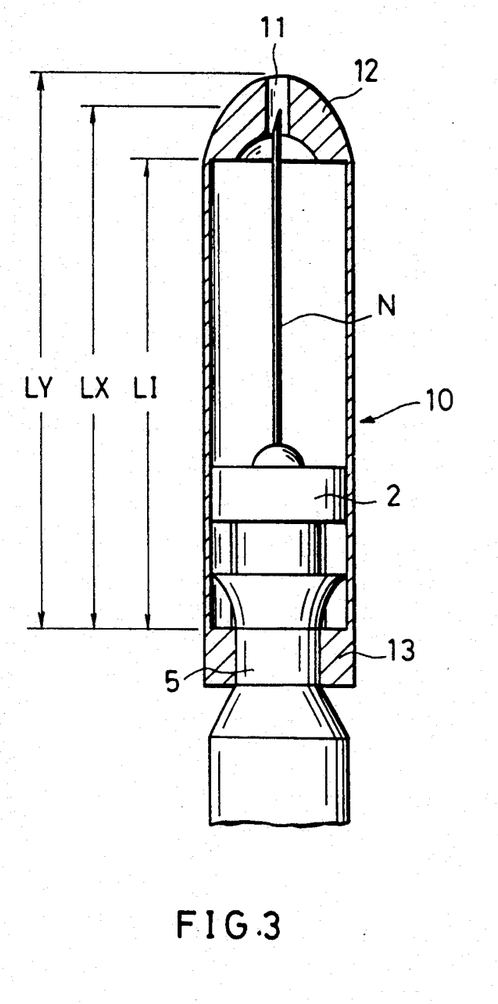

FIG. 3 presents another embodiment of a needle under the present invention. By making the length of the cap 10 short, the tip of cannula N in this embodiment is made to stay inside the bore 11 of the head 12 of the cap 10 when the flange 13 of the cap 10 is engaged with the second neck 5. That is, the distance LX from the tip of the cannula N to the upper end of the second neck 5 is made longer than the length LI of the internal surface of the cap 10 but shorter than the distance LY between the tip of the cap 10 and the upper end of the second neck 5. It is ensured in this structure that the tip of the cannula N passes through the bore 11 when the cap 10 is pressed down.

In the foregoing, embodiments are shown which protect the tip of cannula N by having the flange 13 of the cap 10 engaged with the external surface of the body 1 of the injection needle at various positions over the body 1. The external surface of the body 1, however, needs not to be circumferential. Further, the engaging part of the cap 10 to the external surface of the body 1 needs not to be annular as the flange 13. It is possible to obtain similar results when the engazing positions on the body 1 are made to have various diameters from the axis and single or plural engaging parts are made inside the cap 10 to engage with the engaging positions on the body 1. Here the cap is made to slide to either direction with some friction before the use of the needle, and is made to settle in the lock position after the use without being able to transfer to any other positions.

FIG. 4A to FIG. 4H present another embodiment of the present invention in the form of so called scalp vein set.

Figure 4A:
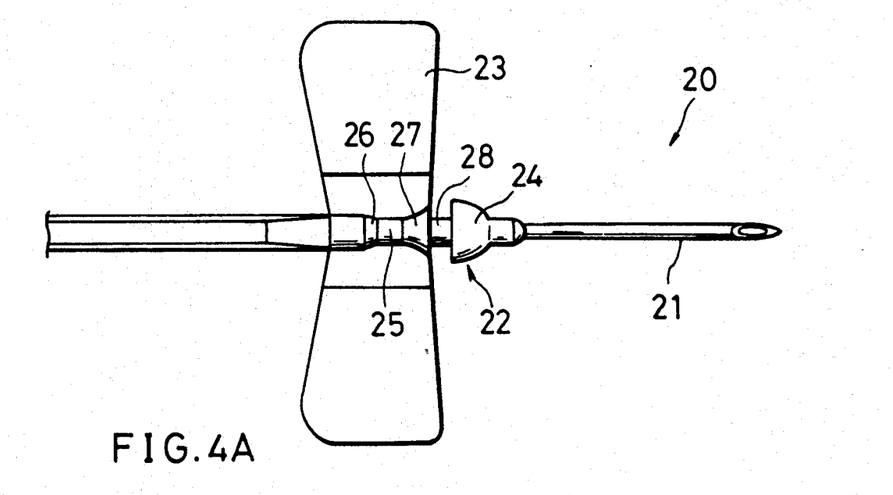
FIGS. 4A to 4H illustrate another embodiment of the present invention applied to a needle for medical use.

FIG. 4A shows the body of a scalp vein set for use in infusion.

Figure 4B:
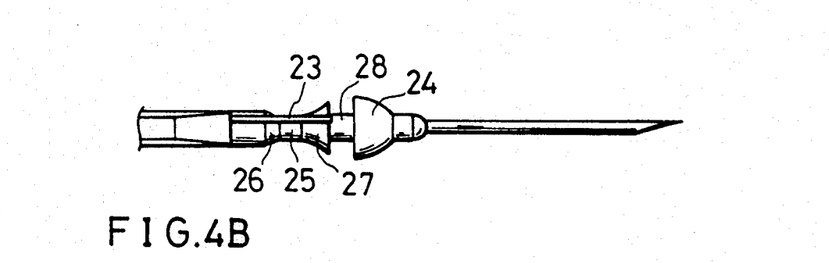

FIG. 4B is a side view of the body shown in FIG. 4A.

The needle part 20 has a cannula 21 and a supporting and connecting member 22 that holds the cannula 21 and connects with other members such as a plastic tube. The cannula 21, for instance, is made of stainless steel having a length of about 15-25 mm with an outside diameter between 0.3-1.2 mm. The tip of the cannula 21 is ground slant and bladed. The supporting and connecting member 22 has wing member 23 to assist puncturing and fixing of the scalp vein set to a living body.

The cannula 21 and the supporting and connecting member 22 are hollow through which medical liquids or other substances flow. The hollow passage may be made by the supporting and connecting member itself or by making the cannula extend to the end of the supporting and connecting member 22.

The supporting and connecting member 22 has a neck 25, and the neck has at the both ends slants 26 and 27 that gradually rise in the directions away from the neck 25. The sliding member, that will be elaborated later, can slide over the slants 26 and 27. The end of the slant 27 in the side of the cannula tip has a sudden diameter change to the neck 28. The both sides of the neck 28 are made perpendicular to the cannula axis, and the sliding member cannot move away once the engaging part falls in the nack 28.

The broad umbrella like part 24 formed at the cannula tip side of the neck 28 functions as a locking wall as well as a device to ease the assembling of the covering member by making the largest diameter larger than the largest diameter in the slant 27.

It is seen in FIG. 4B a wing member 23 running horizontally through the slant 26, the neck 25 and the slant 27.

Figure 4C:
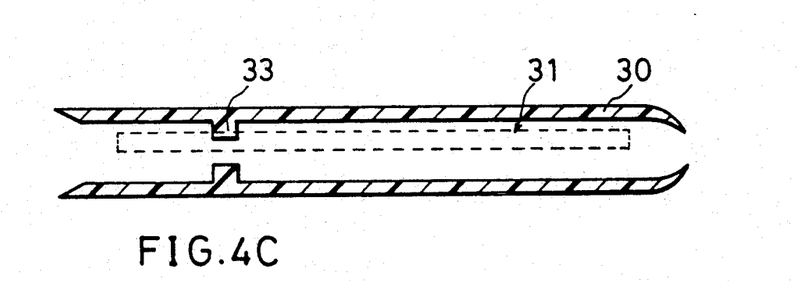
Figure 4D:
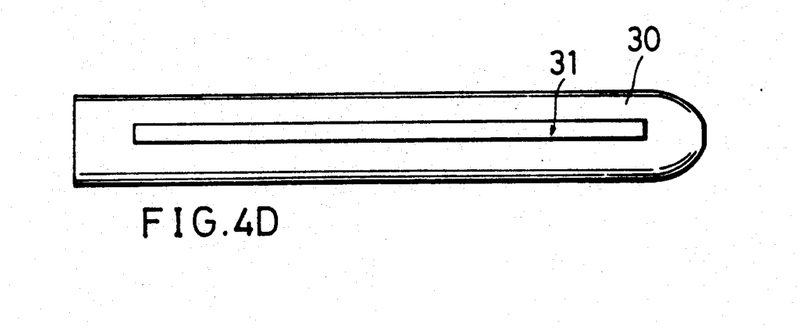

FIGS. 4C and 4D show respectively a cross section and appearance of a covering member 30 that is to be assembled with the needle part of the scalp vein set presented in FIGS. 4A and 4B.

The covering member 30 has openings 31 at the both sides to guide and slide along the wing member 23.

Projection 33 is made in a single or plural points or along the internal circumference of the covering member 30 to engage with the surface of the supporting and connecting member 22 of the needle part 20. The projection 33 has approximately vertical sides against its sliding directions. The projection is also made to produce stable, meta-stable, and sliding positions as it slides and engages with the surface of the supporting and connecting member 22 and the member connected to the tail of the supporting and connecting member 22.

The supporting and connecting member 22, the wing member 23, and the covering member 30 may be made of such materials as polyvinylchloride, ABS resins, polypropylene, polyethylene, and polycarbonate.

Figures 4E, 4F:
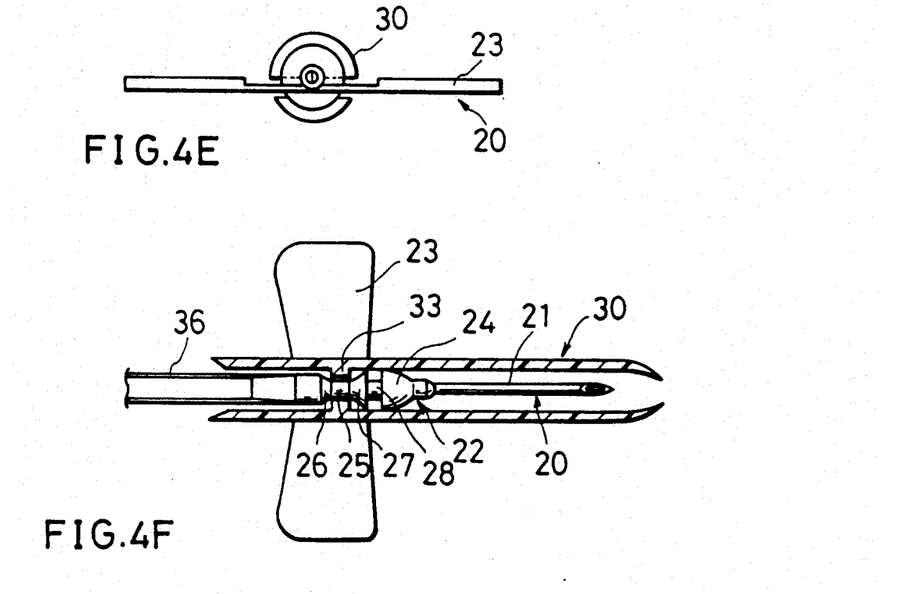

FIG. 4E shows connection of the needle part 20 assembled with the covering member 30.

Figure 4G:
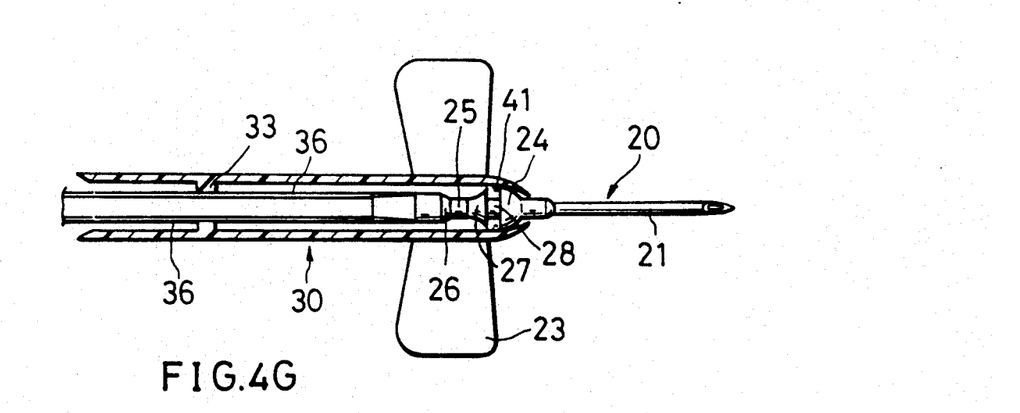
Figure 4H:
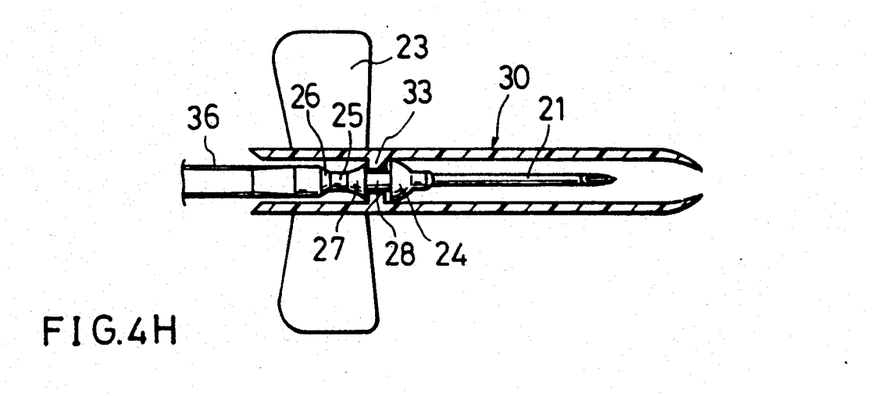

FIGS. 4F, 4G, and 4H show partly cross-sectioned top views of three ststes of the covering member 30 engaging with the needle body 20 and other functional member 36 such as plastic tubes connected to the needle part 20.

FIG. 4F presents the scalp vein set before the use. The set is sterilized, packed, and delivered to hospitals in this state. The covering member 30 is designed to sufficiently cover the cannula 21 of the needle body 20 to prevent the tip from accidentally puncturing in case any persons including the users such as doctors and nurses touch the tip of the covering member 30. The projection of the covering member 30 is engaged with the neck 25 of the supporting and connecting member, and is in a meta-stable position. That is, it needs some frictional force to move the covering member 30 to either of the direction, and the frictional force is made large enough to make the state appear sufficiently stable. A plastic tube 36 is connected to the supporting and connecting member 22, and medical liquid can be supplied to the cannula 21. The internal corner at the tail of the covering member 30 may be made slant to facilitate smooth sliding along the plastic tube 36. The broad umbrella like part 24 touches the inside of the covering material 30 to stabilize the covering member 30.

FIG. 4G shows the state for making use of the needle. It is necessary to expose the cannula 21 of the scalp vein set to use the needle. For this the covering member 30 is moved in the Figure to the left along the axis of the cannula 21, and the projection 33 slides over the slant 26 with some frictional force and further to the left. As the covering member moves to the left, the cannula 21 of the scalp vein set is exposed. The moving distance of the covering member 30 is regulated by the length of the opening 31 located at the side of the covering member 30. In FIG. 4G, the projection 33 of the covering member 30 touches the surface of the plastic tube 36 connected to the supporting and connecting member 22 and the broad umbrella like part 24 also touches the internal surface of the covering member to stabilize the state. To better settle the covering member 30 in this state, something like the stoppers 41 in FIG. 4G may be made to settle against the perpendicular side of the broad umbrella like part 24. Such stoppers may give clicking feeling as the covering member 30 settles in the position in FIG. 4G.

After the use of the medical needle, the needle is pulled out of the skin of the living body. Sharp blades of the cannula 21 is exposed when pulled out, and the blades are liable to injure any nearby persons including doctors and nurses and to transmit pathogens or diseases.

FIG. 4H shows the stable and protected state obtained by sliding the covering member 30 after the use of the medical needle. This state is obtained by sliding the covering member 30 to the full right. The projection 33 inside the covering member 30 slide down the slant 26, through the neck 25, over the slant 27 to finally settle in the stable neck 28 where the projections 33 are locked by the perpendicular sides at the both sides. The covering member 30 is in FIG. 4H restricted to move as the perpendicular sides of the projections 33 are held between the perpendicular sides of the supporting and connecting member 22.

Figure 5A:
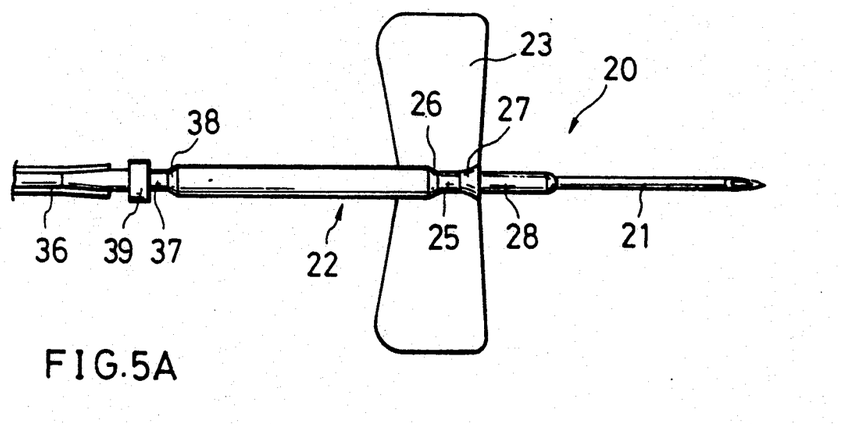
FIGS. 5A to 5D demonstrate another embodiment of the present invention applied to a needle for medical use.
Figure 5B:
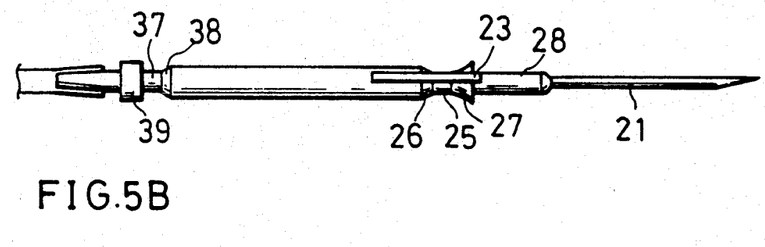
Figure 5C:
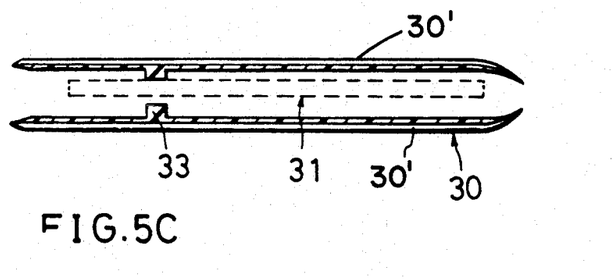
Figure 5D:
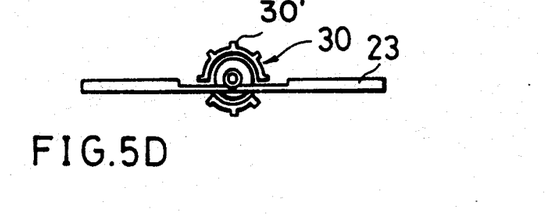

FIGS. 5A-5D show another scalp vein set according to another embodiment of invention. FIG. 5A is a top view of the needle part of the scalp vein set, and FIG. 5B is a side view. FIG. 5C is a cross section of the covering member, and FIG. 5D is a cross section of the covering member connected to the needle part.

When compared with the embodiments shown in FIG. 4A-4H, the present embodiment has another but uni-directional meta-stable position consisting of the neck 37, the slant 38, and the stopper 39 at the end of the supporting and connecting member 22 near to where it is connected to a plastic tube 36. Also in this embodiment, a number of ribs 30' are made to run along the length direction on the covering material 30 to reinforce the covering member against bending.

As discussed, the needle part and the covering member produce meta-stable and stable states according to the relative positions. It takes some frictional force to move out of the meta-stable state, and the force is less to move back to the meta-stable state. The meta-stable state therefore appears to be stable. Once the covering member moves out of the meta-stable state to settle in the stable state after having passed through the slant part, it is locked in the state without being able to move back. Also, the covering member 30 is resticted from rotating around the supporting and connecting member. This also helps to stabilize the handling of the medical needle after the use.

It may look that the covering member 30 is free to move to the right as no broad umbrella like part exists at the right side of the necl 28. By the opening 31 through which the wing member 23 in the needle part 20 projects, the covering member 30 is not able to move more to the right once the projection 33 settlesin the neck 28. That is, the neck 28 provides an irreversible stable state for the covering member 30.

Further, ribs may be made on the supporting and connecting member of the needle part similarly to what has been seen in the covering member.

FIG. 6A-6D show another embodiment of needle.

Figure 6A:
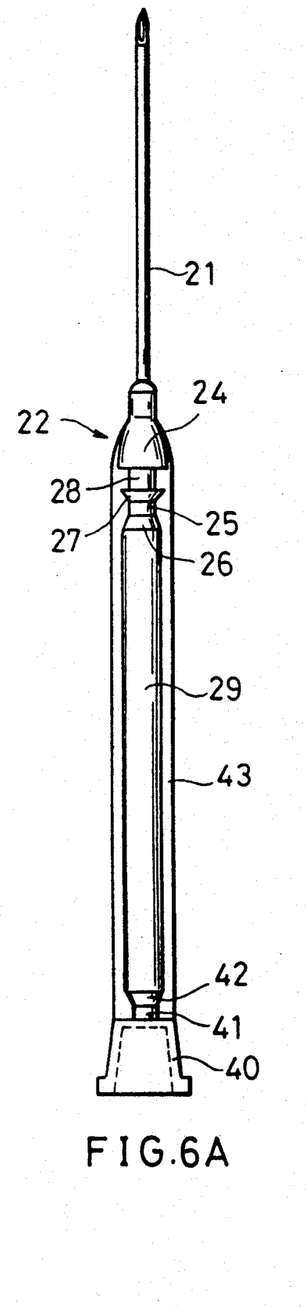
FIGS. 6A–6D present another embodiment of the present invention applied to a needle for medical use.
Figure 6B:
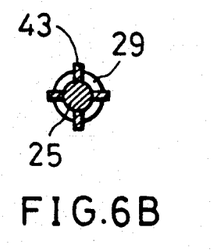
Figure 6C:
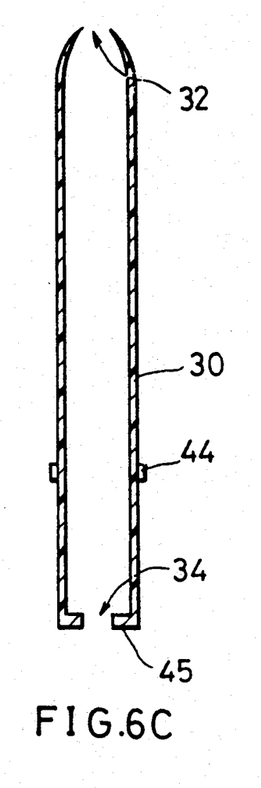

FIGS. 6A and 6B, the supporting and connecting member 22 that holds the cannula 21 and connects with other members possesses, as in the embodiment in FIG. 2, a neck 25 to provide a meta-stable position, slants 26 and 27 at the both ends of the neck 25, and a neck 28 to provide the stable position. The broad body 29 after the slant 26 runs to the longitudinal direction as far as to the other slant 42, neck 41, and the bottom 40. The bottom 40 functions as a stopper as well as a connecting member. A plural number of ribs 43, four ribs for instance, are made to project around the circumference of the supporting and connecting member 22 and to run along the longitudinal direction. The central rib is not shown in FIG. 6A. FIG. 6B shows a cross section of an embodiment having four ribs projecting around the circumference. FIG. 6C shows a covering member to be connected with the needle part.

The covering member 30 possesses an opening 32 at one end to let the cannula 21 pass, and is equipped with flange 45 at the other end to engage with the supporting and connecting member 22. At the bottom of the covering member 30 slit(s) may be formed along the length direction, although not shown in the Figure, to obtain easier elastic transformation. The anti-slip member 44 may be made around the circumference on the surface to ease the handling against slip, as shown in the FIG. 6C.

Figure 6D:
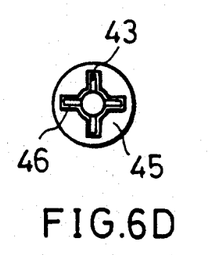

The flange 45 engages with the supporting and connecting member 22 as shown in FIG. 6D. That is, gutters 46 are positioned to receive the ribs to keep the covering member from turning around the longitudinal axis.

The user of the needle may hold the area around the anti-slip member 44, and uncover and cover the cannula 21 by sliding the covering member along the length axis to use the needle safely.

Figure 7:
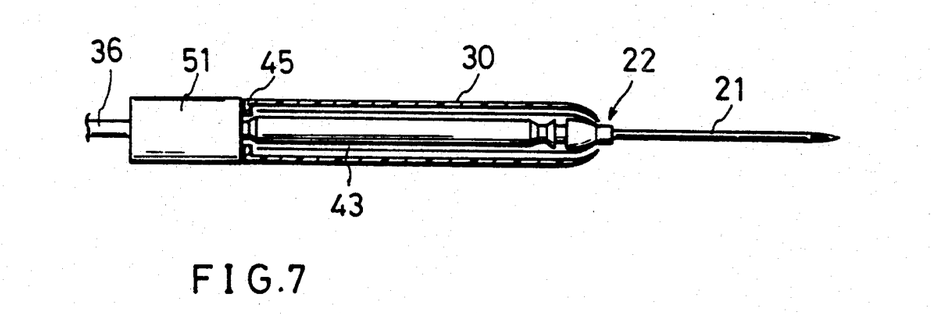
FIGS. 7 and 8 are partly sectional schematic views of other embodiments of the present invention applied to other types of needles for medical uses.
Figure 8:
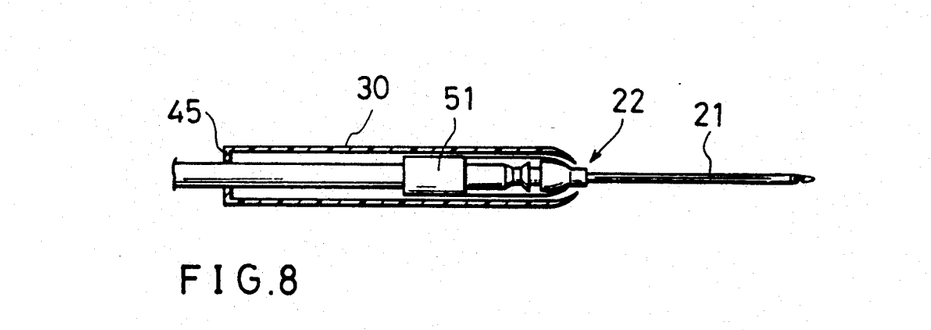

FIGS. 7 and 8 present embodiments similar to that in FIGS. 6A-6D. embodiments may be used in the collection of blood. The needle part, for instance, connected to a plastic tube 36 that brings blood to a blood bag.

The supporting and connecting member 22 that holds the cannula 21 in FIG. 7 is structured the same as that in FIG. 6A except that the bottom 40 is changed to a connector. The covering member 30 may be made in the same structure as that in FIG. 6C. The anti-slip member may by added as in FIG. 6C. A rectangular connector 51 is positioned at the end of the supporting and connecting member 22, and the needle may be punctured by holding by hands the connector 51 and the covering member 30. The section of the supporting and connecting member is structured as shown in FIG. 6B.

The supporting and connecting member has the ribs, and is made hollow to provide optimum volume of flow. As said in the foregoing, the hollow structure may be obtained by making the supporting and connecting member itself hollow or by having the cannula to stretch to the connector 51.

The flange 45 of the covering member 30 is made to have a section as shown in FIG. 6D. The flange 45 has gutters 46 to receive the ribs 43. By making the ribs 43 and the gutters 46 engage each other, the covering member 30 is restricted from rotating.

The covering member 30 may be made to encase the connector 51 as in FIG. 8, by making short the supporting and connecting member 22 and small the connector 51, so that it may slide over the plastic tube. Although not shown in FIG. 8, a projection may be made on the connector 51 to project through and out the covering member 30, like the wing member in FIG. 4F, to form a grip on the supporting and connecting member to ease the sliding of the covering member 30.

The present invention may be used in the dental needles and the vacuum blood collecting needles by applying similar structural concepts to the plastic member.

In the foregoing embodiments, engaging parts are made to project along the internal surface of the covering member, and the surface of the cannula supporting and connecting member is transformed to receive the engaging parts to jointly produce stable and meta-stable positions. The projections of the covering member and the transformation of the supporting and connecting member, however, may be made conversely.

Figure 9:
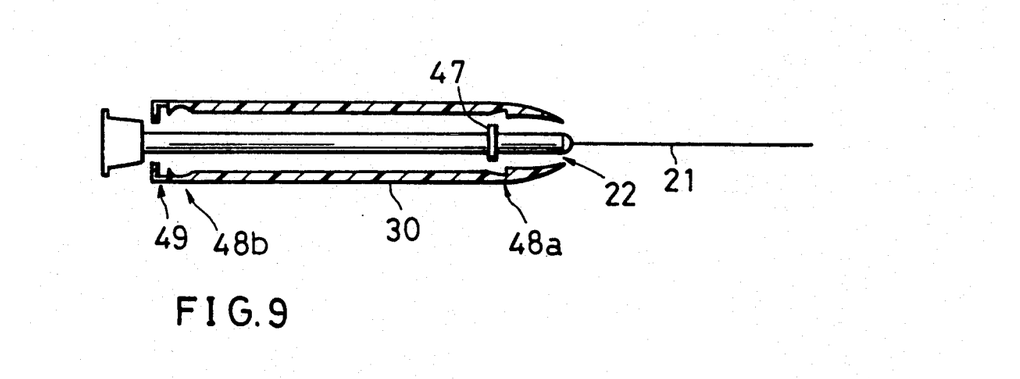
FIG. 9 shows another embodiment of the present invention applied to a medical needle.

The covering member and the supporting and connecting member in FIG. 9 are an example of such a converse formation.

The supporting and connecting member 22 holding the cannula 21 has one projection 47 along the circumference. The covering member 30 has notches 48a and 48b to engage with the projection 47 and to produce meta-stable positions. It further has a notch 49 to produce the stable position.

When the projection 47 is settled at the notch 48a or 48b, the covering member is in its meta-stable position as it may move away from the position in the direction of the adjacent slope. The covering member 30 is no more able to change its position once the projection 47 is engaged with the notch 49 which possesses perpendicular sides at the both ends.

Figure 10A:
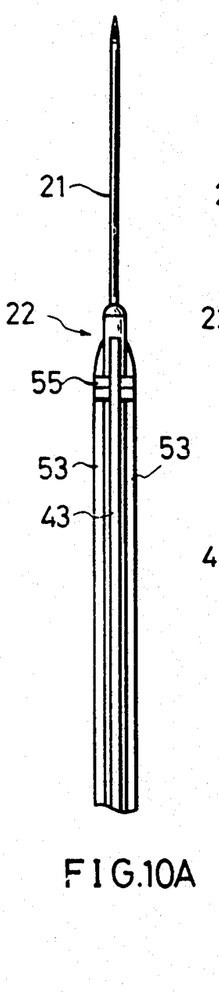
Figure 10B:
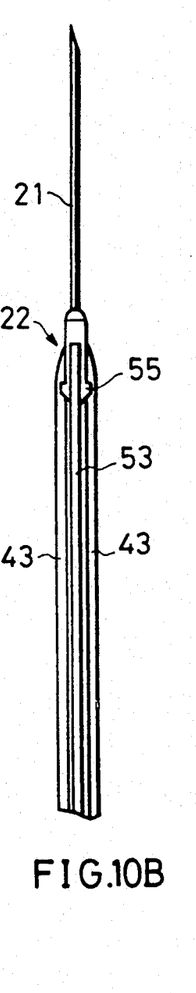

More of the conversely made embodiments such as shown in FIG. 9 are shown in FIGS. 10A to 10D, FIGS. 11A to 11E, and FIGS. 12A to 12E. In these embodiments, the projection is made on the surface of the supporting and connecting member. FIGS. 10A and 10B are the top view and side view respectively of a needle for medical use having projections on the ribs.

Projections of arrow feather shape are formed on a pair of ribs 53. A broad umbrella like part 24 such as that in FIG. 6A may be formed over the projections 55 for convenience of the assembling, but it is not shown in the Figures. This also applies to the embodiment in FIGS. 11s and 12s.

Figure 10C:
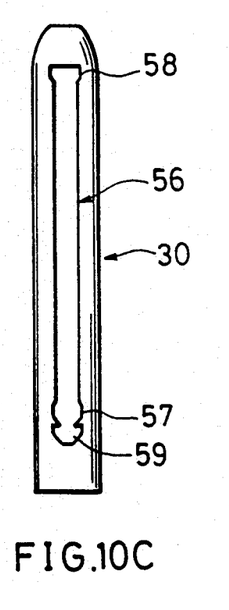

The covering member 30 that engages with the needle part in FIGS. 10A and 10B is shown in FIG. 10C. An opening 56 is seen in the covering member 30, and the opening 56 is made wide at 57, 58, and 59 to receive the arrow feather shape projection 55 in a meta-stable and a stable state. The wide openings 57 and 58 organize meta-stable state, and have slants to let the projections move in both directions. The wide opening 59 forms the stable state with perpendicular sides at the both sides.

Figure 10D:
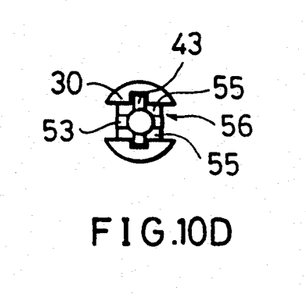

When the covering member in FIG. 10C is assembled to cover the needle part in FIGS. 10A and 10B as shown in FIG. 10D, the covering member 30 is in the meta-stable state at the wide openings 57 and 58 and in the stable state at the wide opening 59.

FIGS. 11A to 11E present another embodiment applied in a scalp vein set.

Figure 11A:
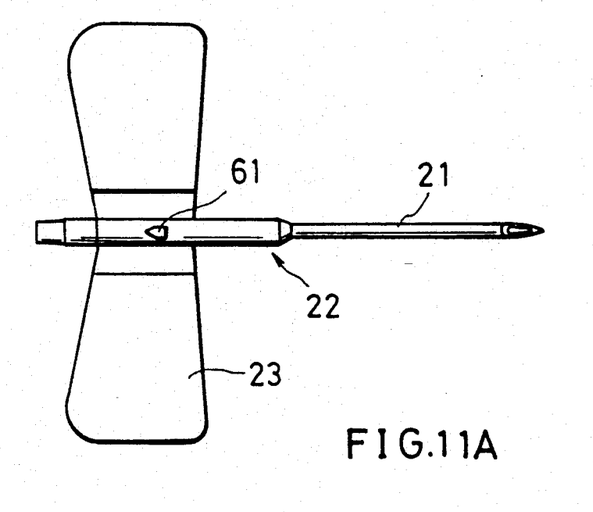
Figure 11B:
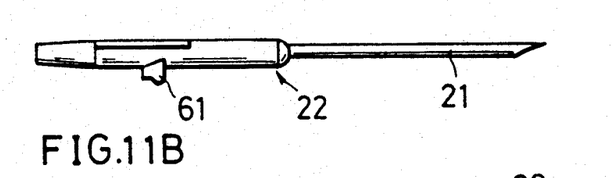
Figure 11C:
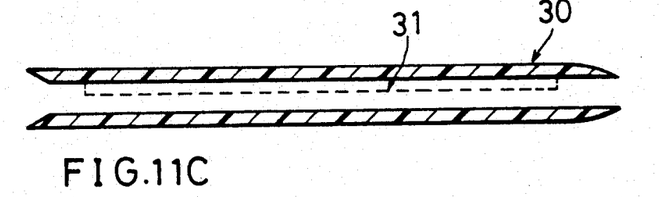
Figure 11D:
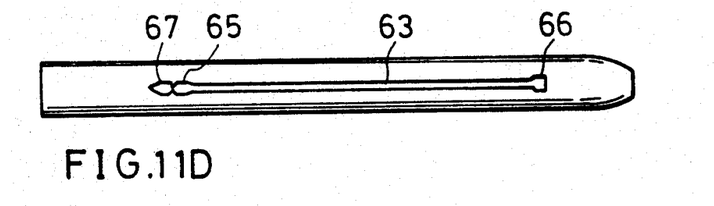

The cannula 21 is held by the supporting and connecting member 22, and the supporting and connecting member 22 has the wing member 23. A projection 61 is formed on the top of the supporting and connecting member. The projection 61 has a pointed end as seen in FIG. 11A. FIGS. 11C and 11D are cross section and top views of the covering member 30 respectively. The covering member 30 has openings 31 at the sides, as shown by the dotted lines in FIG. 11C, to have the wing member 23 pass there through. Further, an opening 63 is made at the top of the covering member 30 as shown in FIG. 11D. The top opening 63 has wide openings at 65, 66, and 67. The right side of the wide opening 67 is perpendicular to the longitudinal axis, and, when the right end of the projection 61 is engaged with the right side of the wide opening 67, the projection 61 is so designed that it does not move back to the adjacent wide opening 65. The projection 61 is able to move away from the other wide openings 65 and 66 in the direction of the slant.

Figure 11E:
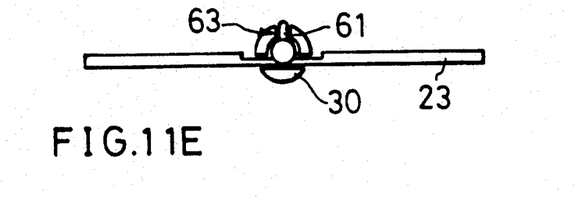

FIG. 11E is a cross section to show the engagement of the needle part and the covering member.

The wing member of the scalp vein set protrudes at the both sides, and the projection 61 stands out at the top. The top opening 63 of the covering member 30 is engaged with the projection 61 to form meta-stable and stable states. When the projection 61 is engaged with the wide opening 65 or 66, it is in a meta-stable position and is able to move away from the position though with some friction. When the projection 61 is fully engaged with the wide opening 67, it is in the lock or stable state and is no longer able to move away from the locked position.

Figure 12A:
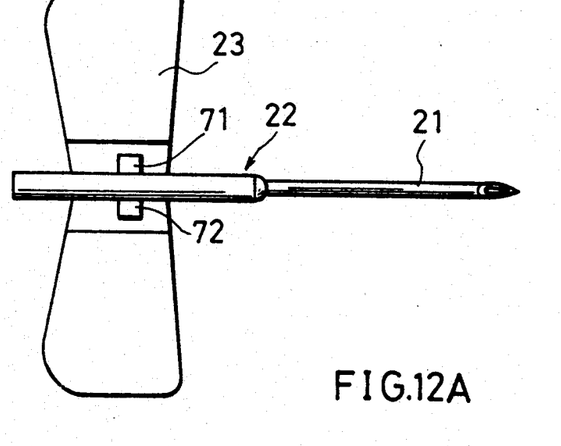
FIGS. 12A to 12E are further embodiments of the present invention applied to other types of medical needles.
Figure 12B:
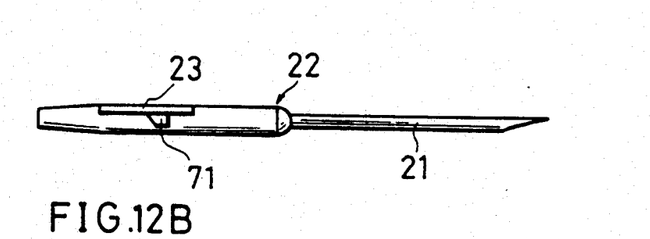
Figure 12C:
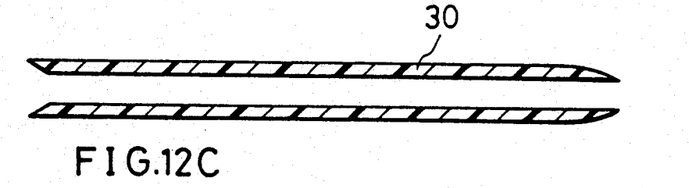
Figure 12D:
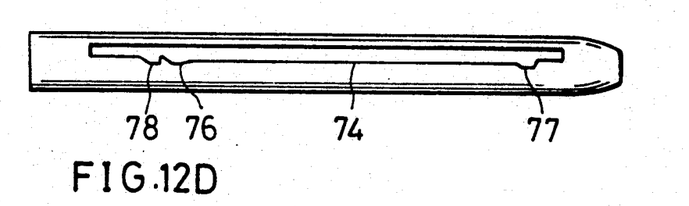
Figure 12E:
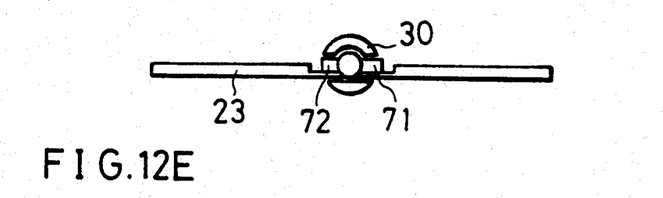

FIGS. 12A-12E a scalp vein set according another embodiment. FIGS. 12A and 12B are the top view and side view of the needle part respectively. Also, FIGS. 12C and 12D are a cross section and a side view of the covering member respectively. FIG. 12E shows a cross section of the needle part with the wing member 23 engaging with the covering member 30.

In the present embodiment, projections 71 and 72 are formed on the wing member 23. The projections 71 and 72 have a slant at one side and a perpendicular side at the other as seen in the projection 71 in FIG. 12B. The openings 74 of the covering member to pass the wing member 23 have wide openings 76, 77, and 78. The wide opening 76 have slants at the both ends, whereas the wide opening 77 has a slant in the moving direction. The wide opening 78 in contrast has a perpendicular end against the longitudinal axis. When the projections 71 and 72 engage with the openings 74, they slide along the openings 74. The projections 71 and 72 form meta-stable state at the wide openings 76 and 77, and are able to move out of the positions in the direction of the slant. The projections in contrast engage with the perpendicular sides of the wide opening 78, and are no longer able to move back once they are fully settled in the state. The stable (or the lock position) is formed in this way.

Structures shown in FIGS. 10A and 10D, FIGS. 11A to 11E, and FIGS. 12A to 12E are similar to that shown in FIG. 9 in that indents are made on the covering member and a projection(s) is placed on the needle part. The structures differ from other structures, however, in that the direction of the force acts in the circumferential direction.

Other structures also be employed as long as the needle supporting and connection member and the covering member engage each other to produce a stable but still transferable meta-stable state and a stable and irreversible state.

As seen in the foregoing, the covering member covers the cannula in the unused and sterile needles for medical uses. By covering the sharp point, the needles prevent accidental punctures to whoever handle or use the needles. The covering member can slide to uncover the cannula, and the needles are used in the same way as the ordinary medical needles. The covering member is moved to the stable position after the use, and is locked at the stable position. The covering member does not reveal the cannula any more once it is settled in the stable position, and completely protects the sharp blade of the cannula. The needles therefore ensure that the sharp points do not accidentally injure hands or fingers of the users and all those handle the needles after use, and until the needles are finally demolished.

Although some embodiments of the present invention have been discussed, the invention is not limited to these embodiments. The needles such as for dialysis, for instance, with or without wings, can be made to prevent accidental punctures by modifying the needles similarly to the embodiments already discussed.

It is also possible to change the needles or the tip of tubes to make protective apparatus by applying the same principles to the needles that are attached to the tips of tubes in such cases as in the infusion and blood transfusion.

The present invention has been described in detail with regard to the illustrated embodiments, but should not be restricted to these embodiments. It should be clear to those skilled in the art that the invention is applicable in a number of ways by various combinations, changes, and improvements.

I claim:

1. A needle for medical use comprising:

a cannula having a longitudinal axis and formed with a sharp blade tip;

a supporting and connecting member holding said cannula at one end of said supporting and connecting member and adapted for connection to another member at the other end of said supporting and connecting member;

a cover member having a surface extending in a circumferential direction, said cover engaged with said supporting and connecting member and movable along said longitudinal axis of said cannula and said supporting and connecting member between a first position where said cover releasably encloses the blade tip of the cannula, and a second position where said cover irreversibly encloses the blade tip of the cannula;

wherein said supporting and connecting member is provided with at least one radially extending projection and wherein said cover is provided with at least a first linear slot, said slot including a main portion extending substantially parallel to said longitudinal axis and including two enlarged areas at one end of the slot, wider in the circumferential direction than said main linear portion of said slot, and adapted to receive said radially extending projection upon linear movement of the supporting and connecting member relative to the cover, said two enlarged areas being adjacent one another and defining said first and second positions;

wherein only a single radial projection is provided on said supporting and connecting member; and wherein a pair of wings extend in radially opposite directions from said supporting and connecting member.

2. The needle of claim 1 wherein said cover is provided with second and third slots for accommodating said wing members.

* * * * *